United States Patent
Sudekum

(10) Patent No.: US 9,149,354 B2
(45) Date of Patent: Oct. 6, 2015

(54) FLEXOR TENDON REPAIR DEVICE

(71) Applicant: Anthony E. Sudekum, O'Fallon, MO (US)

(72) Inventor: Anthony E. Sudekum, O'Fallon, MO (US)

(\*) Notice: Subject to any disclaimer, the term of this patent is extended or adjusted under 35 U.S.C. 154(b) by 2 days.

(21) Appl. No.: 13/946,607

(22) Filed: Jul. 19, 2013

(65) Prior Publication Data

US 2014/0024885 A1    Jan. 23, 2014

Related U.S. Application Data

(60) Provisional application No. 61/673,827, filed on Jul. 20, 2012.

(51) Int. Cl.
| | |
|---|---|
| *A61F 2/00* | (2006.01) |
| *A61B 17/06* | (2006.01) |
| *A61B 17/11* | (2006.01) |
| *A61F 2/08* | (2006.01) |

(52) U.S. Cl.
CPC ......... *A61F 2/0063* (2013.01); *A61B 17/06166* (2013.01); *A61B 17/11* (2013.01); *A61B 17/1146* (2013.01); *A61F 2/0811* (2013.01)

(58) Field of Classification Search
CPC .. A61B 17/1146; A61B 17/11; A61F 2/0063; A61F 2002/0068
USPC .............................................. 623/13.11–13.2
See application file for complete search history.

(56) References Cited

U.S. PATENT DOCUMENTS

| | | | |
|---|---|---|---|
| 3,842,441 A | 10/1974 | Kaiser | |
| 4,400,833 A * | 8/1983 | Kurland | ..................... 623/13.17 |
| 4,469,101 A | 9/1984 | Coleman | |
| 5,362,294 A * | 11/1994 | Seitzinger | ....................... 600/37 |
| 5,723,008 A | 3/1998 | Gordon | |
| 5,800,544 A | 9/1998 | Demopulos | |
| 6,090,996 A | 7/2000 | Li | |
| 6,102,947 A | 8/2000 | Gordon | |
| 8,858,577 B2 * | 10/2014 | Kubiak | ......................... 606/151 |
| 2009/0024147 A1 | 1/2009 | Ralph | |
| 2011/0307059 A1 | 12/2011 | Young | |
| 2012/0010708 A1 | 1/2012 | Young | |
| 2012/0010727 A1 | 1/2012 | Young | |
| 2012/0020933 A1 | 1/2012 | Young | |
| 2012/0226296 A1 | 9/2012 | Bindra | |
| 2013/0261542 A1 * | 10/2013 | Elachchabi et al. | ........ 604/93.01 |

\* cited by examiner

*Primary Examiner* — Thomas J Sweet
*Assistant Examiner* — Daniel Bissing
(74) *Attorney, Agent, or Firm* — Charles McCloskey

(57) ABSTRACT

A flexor tendon repair device has a sheet of mesh material of rectangular shape with four edges: two longitudinal edges and two lateral edges perpendicular to the longitudinal edges. Each pair of edges is mutually parallel and spaced apart. Each edge is also folded inwardly for two smooth edges upon which the healing tendon rests and two smooth edges where the sheet mutually joins. Along with the sheet, the invention includes sutures, typically doubled, and one at each lateral edge. The lateral edges generally support the healing tendon while the sheet wraps around the tendon with the longitudinal edges generally parallel to the length of the tendon. A surgeon, during use of the invention, tightens each suture along the longitudinal edges, closing the device, and then upon the laterals to tie the suture. Upon tying, the mesh attains an ovoid shape similar to the natural cross section of a tendon.

8 Claims, 5 Drawing Sheets

FLEXOR TENDON REPAIR DEVICE

CROSS-REFERENCE TO RELATED APPLICATION

This non-provisional application claims priority to the pending provisional application 61/673,827 filed on Jul. 20, 2012 which is owned by the same inventor.

BACKGROUND OF THE INVENTION

The flexor tendon repair device generally relates to orthopedic devices and more specifically to a tendon enwrapping device. More particularly, the invention wraps and compresses two tendon ends joined in a repair.

Effective repair of flexor tendons has long been a significant problem and remains unresolved within the realm of hand surgery. The pursuit of a secure, relatively simple, inexpensive surgical technique and device to assist and facilitate the effective repair of flexor tendons still eludes hand surgeons and the practice and advancement of hand surgery in general.

The problems which must be addressed in any flexor tendon repair technique and device include creation of a connection, co-aptation or union of the two cut ends of the flexor tendon, usually utilizing suture or other material to connect one side of the injured tendon to the other. This typically involves passing sutures through both sides of the lacerated tendon and then tying two or more free ends of the tendon suture together, holding the cut ends together. Various suturing techniques are used including a variety of crisscross patterns, looped sutures, locking sutures, and the like. A proper tendon repair must create a repair between the two cut ends of the tendon strong enough to withstand the forces involved in muscle contraction, such as for finger movement. Many of the existing repair techniques and the treatment of flexor tendon injuries involved the use of four, six, or eight suture strands which are passed through the tendon core to provide adequate "strength of repair." Because multiple strands of suture pass through the "core" of the tendon, this also brings about multiple knots to secure the cut tendon ends. These knots, placed on the outside of the tendon, frequently become a source of irritation and adhesions to the surrounding soft tissues. When tendon adhesions occur, then "excursion," or movement of the repaired flexor tendon as it passes through the retinacular "pulley" system has significant inhibition or restriction.

Another option includes placing the knots inside the tendon, at the site of the laceration and co-aptation. Unfortunately, in this location the "core" sutures and knots can impede and interfere with the natural repair process because these knots sit between the two cut ends of the tendon which must heal and grow together. As above, patients require a strong repair but also a flexor tendon that must also move. Medicine has learned that the sooner movement of the tendon begins after the repair, the better. This movement serves to prevent and/or minimize adhesions and maximize excursion.

While the strength of the repair may be addressed by utilization of stronger and more numerous suture strands, the prior art has overlooked and not addressed the bulk of the repaired flexor tendon at the site of the repair. This bulkiness prevents movement and excursion of the repaired flexor tendon, often because of fraying of the lacerated tendon ends, or hydration and swelling of the cut ends after an injury. Multiple sutures and knots at the repair site, as well as the "accordion effect" associated with tendon re-approximation also contribute to the "fat repair site" which severely limits excursion and ultimately results in a poor functional result. Re-approximation occurs where the two cut ends are drawn together so that the tendon ends are compressed longitudinally and "bunched." The end result of a bulky repair site causes the site of the tendon repair to have a significantly larger, bulkier, and more irregular shape than the natural uninjured tendon. This bulkiness has a profound negative effect on the ability of the repaired flexor tendon to move through the flexor tendon retinaculum system. The flexor tendon must pass through a relatively narrow "tunnel" of fibro-osseus tissue which extends from the metacarpophalangeal, or MP, joint proximally to the distal interphalangeal, or DIP, joint distally. Tendon movement through this tunnel is referred to as "tendon excursion". This region is known as "no man's land" and "zone 2" by orthopedic practitioners.

The term "no man's land" arose from early surgeons who indicated that primary repair of flexor tendons in this region could not be performed successfully and therefore delayed secondary repair or performed no repairs. This pessimistic approach came about because the practitioners' experience of the repairs in this zone consistently failed due to adhesions and tendon rupture.

Medicine has the goal of a flexor tendon repair being strong enough to withstand early, or immediate, active movement of the tendon and finger after the repair. As long as early active motion begins early after the repair, then the risk of tendon adhesions reduces significantly. However, as noted above, early active motion requires a strong repair and minimum friction between the site of the repair and the surrounding retinacular pulley system, through which the tendon must pass. The repair technique must also reduce and minimize bulk (due to poor repair technique and bunching) at the site of the coaptation. Decreasing the bulk of the repair will prevent the tendon from getting "hung up," or stuck, within the retinacular tunnel. The repair must have enough strength for immediate active motion and also to create a relatively tapered, compressed repair site which will minimize friction and allow for maximize tendon excursion through the retinacular tunnel.

DESCRIPTION OF THE PRIOR ART

Over the years, physicians, technicians, and device makers have built and used various tendon repair devices and methods, particularly for the fingers of the human hand. There are many suture repair techniques and devices which have been used, proposed and/or developed which have attempted to address the structural, physical, anatomic, dynamic and a functional aspects of lacerated flexor tendons which must be considered to achieve consistently good functional results with flexor tendon repair techniques.

For centuries though, people have made and played with a Chinese finger trap. The finger trap works as follows. The tightening of the trap is simply a normal behavior of a cylindrical, helically wound braid, usually the common biaxial braid. Pulling the entire braid lengthens and narrows it. The length is gained by reducing the angle between the warp and weft threads at their crossing points, but this reduces the radial distance between opposing sides and hence the overall circumference. The more one pulls, the more the circumference shrinks, that is, the trap tightens.

Also, practitioners have used Prolene® sutures from Ethicon® of Johnson and Johnson® to perform various Thread-lift® procedures. These procedures have utilized sutures to suspend soft tissue into a more cosmetically pleasing appearance for a patient. These sutures have barbs upon their ends that embed into the soft tissues, securing the sutures against axial loads. These sutures then allow upward lifting of the tissue.

The prior art also includes helical anchors, usually of metal, threaded into the ends of a severed tendon. Two anchors are used for each tendon and connected using a wire. The surgeon pulls the tendon ends to a desired position and then fixes the wire at that length. This metallic tendon repair becomes a permanent part of the patient and has some risk of rejection or working outwardly from the tendon and interfering with the operation of the joint under repair. The prior art also has embedded spines that bridge the gap between severed tendon ends. The spine has two ends with spaced apart ribs that extend at an angle to the spine. Each end has ribs extending outwardly in opposite directions so that upon pulling of the tendon, the spine remains in place. The spine and its ribs allow for insertion into the tendon ends but not removal. The ribs allow for one way installation. Both the anchors and the spines allow for the tendon to regrow across the severance between the ends. Akin to the helical anchors, the spines insert deep into tendon tissue putting that tissue at risk for mechanical degradation.

The present invention overcomes the disadvantages of the prior art and provides a flexor tendon repair device that wraps and compresses a repaired tendon into an ovoid cross sectional shape, more particularly an elliptical cross section, so that the healing tendon moves lengthwise without impeding a nearby joint. The present invention provides a device the supports the structure of a healing tendon with minimal increase in tendon volume proximate a constricting joint tunnel. The present invention provides a device with folded edges that lead to a smoother interface between the healing tendon and the invention. The present invention accomplishes these goals of a strong, stable tendon repair capable of immediate use without increased bulk.

SUMMARY OF THE INVENTION

Generally, the flexor tendon repair device has a sheet of mesh material having a generally rectangular shape with four edges: two longitudinal edges and two lateral edges perpendicular to the longitudinal edges. The sheet may be of a mesh like construction as well. Each pair of edges is mutually parallel and spaced apart. Each edge is also folded inwardly which presents two smooth edges upon which the healing tendon rests and two smooth edges where the sheet mutually joins upon enwrapping the tendon. Along with the sheet, the invention includes sutures, typically doubled, and one at each lateral edge. The lateral edges generally support the healing tendon while the sheet wraps around the tendon with the longitudinal edges generally parallel to the length of the tendon. A surgeon, during use of the invention, tightens each suture upon the laterals and then ties the suture. Upon tying the suture, the mesh attains a generally ovoid, or elliptic or elliptical, shape that cooperates with the natural cross section of a tendon.

There has thus been outlined, rather broadly, the more important features of the invention in order that the detailed description thereof that follows may be better understood and that the present contribution to the art may be better appreciated. The present invention also includes a semi-rigid spine, undulating longitudinal edges for merging to sides of the invention, loops to assist the surgeon during suturing, a helically wound suture for additional compression, and loops extending outwardly from an edge. Though this description refers to a tendon in many places, the invention may see use upon ligaments, nerves, and other slender, elongated body parts of people and select animals. Additional features of the invention will be described hereinafter and which will form the subject matter of the claims attached.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

One object of the present invention is to provide a flexor tendon repair device that grips and compresses a tendon.

Another object is to provide such a flexor tendon repair device that allows for passage of the invention installed upon a tendon through the adjacent tunnel.

Another object is to provide such a flexor tendon repair device that a surgeon may install with a minimum of equipment.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

DESCRIPTION OF THE PREFERRED EMBODIMENT

Figure 1:
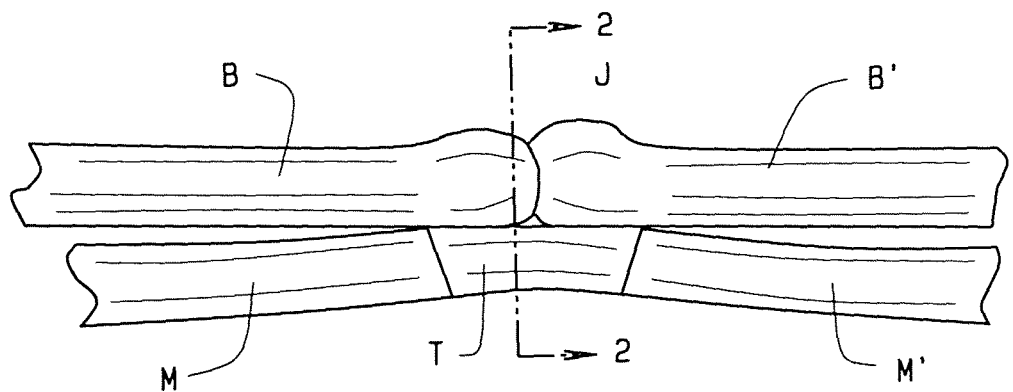
FIG. 1 provides a side view of a finger joint.

The present art overcomes the prior art limitations by providing a flexor tendon repair device. The "Tendon Trap" Tendon Repair Device is composed of a resorbable or nonabsorbable suture material which is constructed in a diagonal crisscrossing, interlocked sheet of material of mesh like construction which has the overall shape of an open or "slit cylinder". The slit in the mesh cylinder is open longitudinally in order to allow the tendon ends to be easily placed within the cylinder, whether the tendon has already been approximated or the cut ends remain unattached. The cylinder thus formed is generally hollow and the device attains an overall tubular form.

The grossly approximated tendon is then placed inside the open "tendon trap" cylinder which wraps around and envelops the tendon repair site. For a standard finger flexor the "tendon trap" extends at least 1 cm proximal and 1 cm distal to the repair site.

Multiple interlocking closed loops line both sides of the open longitudinal slit. Two double-ended sutures with tapered curved needles on either end are passed back and forth from one side of the slit to the other through the closed loops on either side, advancing distally with each pass, much like lacing a shoe, and then tying the laces on both ends. The sutures have sufficient strength to withstand and to carry the load of a tendon, ligament, or other body part placed into the invention. The sutures also resist separation of the ends of the body part when in motion and placed into the invention. This construct will be used to "cinch" and tighten the tendon trap mesh around the tendon repair site as well as at least one cm proximal and distal (as with a girdle around the waist or tennis shoe around the foot).

As the "free ends" (with still attached curved needles, or sutures) are tightened, the tendon is compressed at the site of the repair and then the free ends are knotted at either end. The compression at the site of the tendon repair is an essential element. The attached needles can then be passed transversely, that is, perpendicularly through the tendon, back and forth at least once on each cut end of the tendon, possibly more passes, depending on the location and tendon type. This weaving of the tendon suture transversely through the tendon trap device, as well as through the tendon core, serves to secure and attach the tendon trap device to both ends of the cut tendon while at the same time compressing the tendon repair in the anterior-posterior, or AP, plane. This AP compression more closely approximates the natural, or normal, tendon demeanor, that is, design, which will greatly facilitate excursion of the repaired tendon through the retinacular system. The initial "holding suture" can then be removed if so desired or left in place if so desired, such that there will be no actual tendon which crosses through the "core" of the tendon at the site of the tendon coaptation. Elimination of the primary core suture serves to minimize any interference of the natural healing which must occur at the site of coaptation. The present invention provides a strong mesh netting of interlocking sutures on the outside of the tendon surface, while the multiple transverse core sutures which also pass through the mesh serve to compress and taper the repaired tendon in such a way that maximum excursion and early active motion is feasible.

The name "tendon trap" is derived from a children's toy called the "Chinese finger trap" which is a cylinder of woven interlocking diagonal woven material, which when placed around one finger on each hand "traps" the fingers and thus the hands together, in such a way that any attempt to pull the fingers out only tightens the trap around the fingers. This feature of the finger trap design incorporates within the design of the present invention, which is the quality of tightening of the cylinder around the tendon whenever axial longitudinal force, is applied to either end. This feature serves to tighten the invention around the repaired tendon whenever any load or force is transmitted to it. Compression of the tendon at the repair site repair will further stabilize the repair and facilitate improved tendon excursion by narrowing the caliber of the repair site.

The tendon repair device could be adapted for effective use in any part of the human body. Though this description refers often to tendons and flexor tendon, the invention may see use upon ligaments and possibly upon nerve tissue. The size of the tendon trap may vary depending on the specific tendon and anatomic location of its use, however at least 1 cm proximal and 1 cm distal to the site of the injury would be required for finger flexor tendon repair. The Applicant foresees that the smallest size would be approximately 2 cm and a largest size of approximately 8 cm to 10 cm for biceps, triceps or Achilles tendon repair. The tendon trap mesh would be a custom designed mesh product manufactured in various sizes as "open lace-able cylinders." Ideally these cylinders would "hold their shape" to facilitate ease of application but all would tighten around and conform intimately to the tendon once applied.

Figure 2:
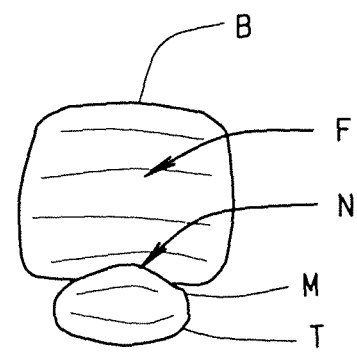
FIG. 2 shows a sectional view through a finger joint outside the face of a knuckle.
Figure 3:
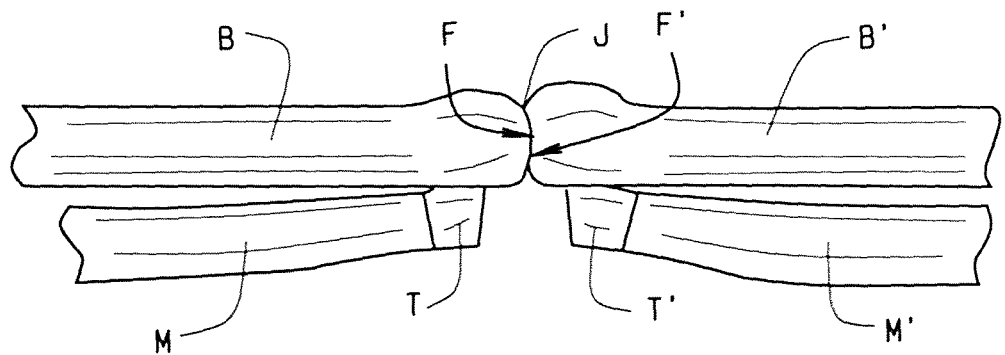
FIG. 3 shows a side view of a finger joint with the tendon severed.

FIG. 1 shows a typical finger joint, as at a knuckle J. The knuckle is shown, the Applicant foresees application of this invention to other joints and skeletal structures that involve tendons. Here shown in the joint, two bones, B, B' appear collinear but have a common joint to allow for angulation. The angulation of one bone relative to the other bone occurs upon operation of adjacent tendon T under the action of its connecting muscle M, M'. To allow for lever action across the joint and bone movement, the tendon extends across the joint through a tunnel N as shown in FIG. 2. The tunnel appears upon the face F of the bone B. The tunnel receives a portion of the thickness of the tendon and allows for passage of the tendon across the joint during movement. The tendon has a generally oval cross section that extends outwardly from the tunnel. However, as described above, a tendon may sever due to an injury or other cause as shown in FIG. 3. Upon severing, the tendon separates into two ends, T, T', as the connecting muscles contract. Once separated, the tendon ends T, T' can no longer operate the joint.

Figure 4:
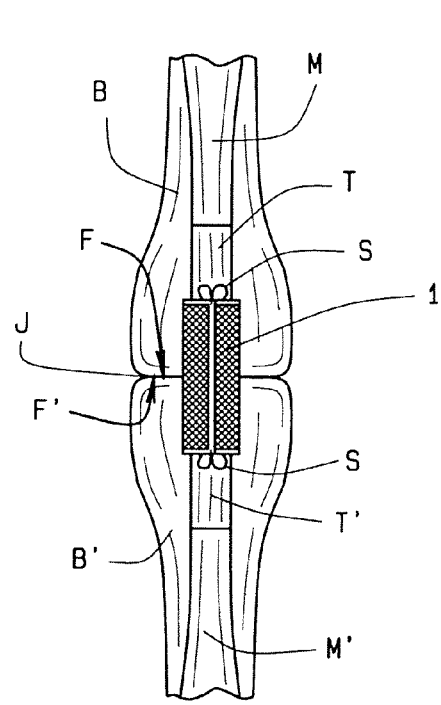
FIG. 4 shows a bottom view of finger joint with the present invention installed.

FIG. 4 then shows the present invention 1 installed upon a tendon T, T' undergoing repair. The present invention receives the ends T, T' into each end of the device and a surgeon secures the device to each tendon end using a transfixion stitch S. The surgeon then closes the device around the tendon and upon itself where the surgeon then stitches it closed. The stitches S and the operation of the invention keep it upon the tendon as the tendon ends heal and naturally reconnect.

Figure 5:
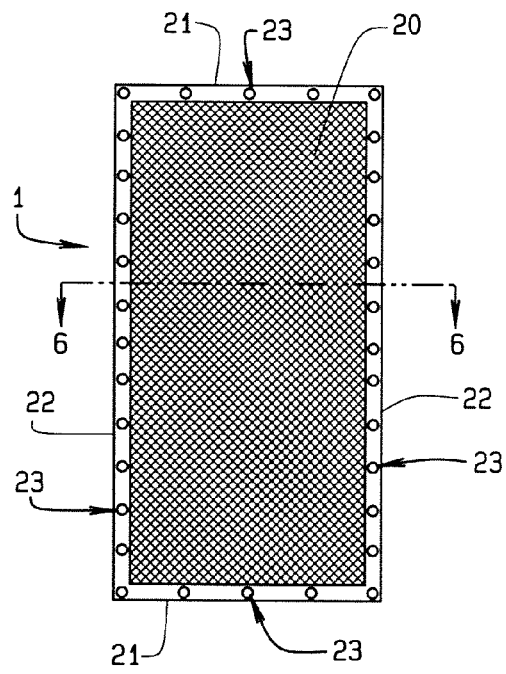
FIG. 5 shows a top view of the present invention.

The invention 1 appears in flat form from the top in FIG. 5. The invention has a generally planar rectangular form with a mesh construction as at 20. The planar form is its first position and the invention generally ships to customers in flat form or the first position. The invention has two mutually parallel and spaced apart lateral ends 21 and two mutually parallel and spaced apart longitudinal sides 22. The lateral ends are perpendicular to the longitudinal sides. Both the lateral ends and the longitudinal sides have a plurality of apertures 23 formed therein. The apertures may be arranged in a pattern. The apertures receive sutures during installation of the invention upon a tendon. The sutures pass through the apertures of both sides and mutually connect both sides similar to lacing upon a shoe. In an alternate embodiment, the apertures include grommets, one grommet per aperture, to reinforce the lateral edge at a puncture. In a further alternate embodiment, the longitudinal sides 22 have reinforcement, such as by folding over or by piping joined to the mesh layer. Also, in another alternate embodiment, the lateral ends 21 have reinforcement too, such as by folding over or by piping joined to the mesh layer.

Figures 6, 7:
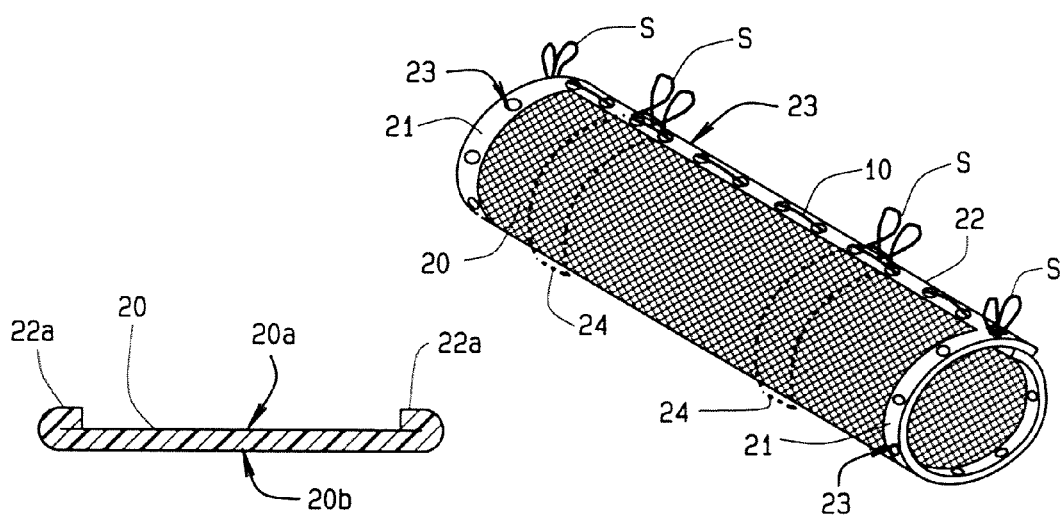
FIG. 6 illustrates a bottom view of the present invention.
FIG. 7 provides an isometric view of the invention rolled.

FIG. 6 shows a sectional view transversely that reveals the construction of the two longitudinal sides 22. This view can also represent the construction of the lateral ends as well. The longitudinal sides are formed by folding a portion of the sheet of mesh material or construction, as at 20 inwardly. The portion is approximately 150% to 400% of the thickness of the material of the invention. The invention has an inner surface 20a that abuts a tendon upon installation and an opposite outer surface 20b that remains outwardly from the tendon. The invention has the folded portions 22a generally upon the inner surface as shown.

Having described the preferred embodiment, FIG. 7 has a surgeon placing it beneath the two severed ends T, T' and inserting the ends approximately 1 centimeter inwardly upon the device, not shown for clarity. The surgeon secures the alternate embodiment of the device to each end of the tendon with a transfixion stitch and then rolls each side 22 of the device upwardly and around the two ends T, T'—of a body part such as a tendon—attaining the cylindrical like form shown in FIG. 7. This form has an ovoid or elliptic shape in cross section and denotes the second position of the invention. The ovoid or elliptic cross section of the invention approximates the natural shape of a tendon or other body part placed into the invention. The ovoid shape has a major axis, or width, to minor axis, or height, of approximately 2.5 to 1, such as in an elliptic cylinder. The surgeon overlaps one longitudinal side 22 over the other side so that they are spaced apart but mutually parallel, such as in an overlapping joint. The surgeon also aligns the overlapped lateral ends 21 so that the lateral ends have a smooth texture transverse the tendon. The surgeon then extends a doubled suture, as at 10, through the apertures 23 along the overlapped sides 22. The surgeon does this suture from both ends 21 of the invention and secures it with a stitch S. The surgeon also performs an additional suture through the mesh of the invention as at 20 and into each cut end of the tendon as at 24 secured with a stitch S. These two sutures through the tendon mechanically connect the tendon repair to the mesh of the invention. With both ends sutured, the surgeon then pulls the sutures snug which closes the left side upon the right side of the invention generally above the tendon, not shown for clarity. The surgeon then takes another double suture and passes it through the apertures 23 along the lateral ends in a generally circular manner and pulls this other double suture and in doing so compresses the material of the device upon the tendon ends therein, or other body parts.

Figure 7A:
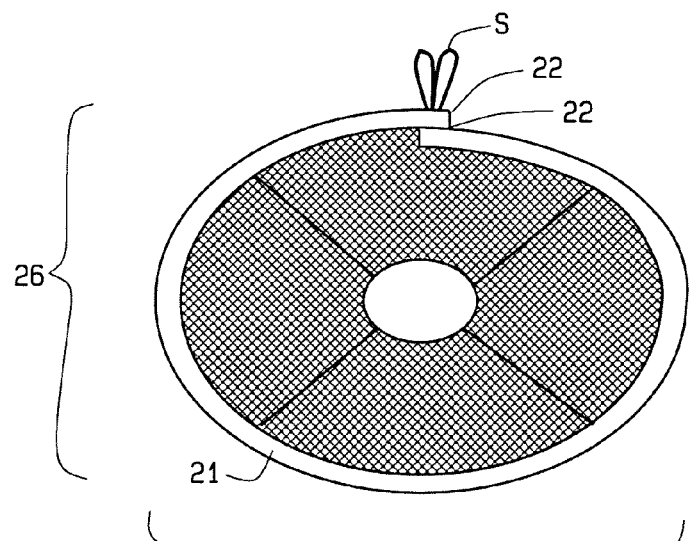
FIG. 7a provides an end view of the invention.

FIG. 7a provides an end view of the invention after installation upon the ends, T, T', of a tendon. The installation wraps the sides 22 upwardly and inwardly upon the tendon for securement in an overlap of the sides with a stitch S as shown. The invention attains an ovoid shape with a major axis, or width, as shown at 25, and a minor axis, or height, as shown at 26. The width is generally perpendicular to the height. The width has a ratio to the height of approximately 2.5 to 1. The ovoid cross section of the installed invention matches the typical tendon cross section. The sides 22 overlap generally centered upon the width of the invention shown on end and upon the minor axis of the cross section, that is, the top. The invention includes a material with a shape memory, with the shape of the tendon cross section imposed upon the material. Though having a shape memory, the invention permits compression and unfolding into flat form for shipping.

Figure 8:
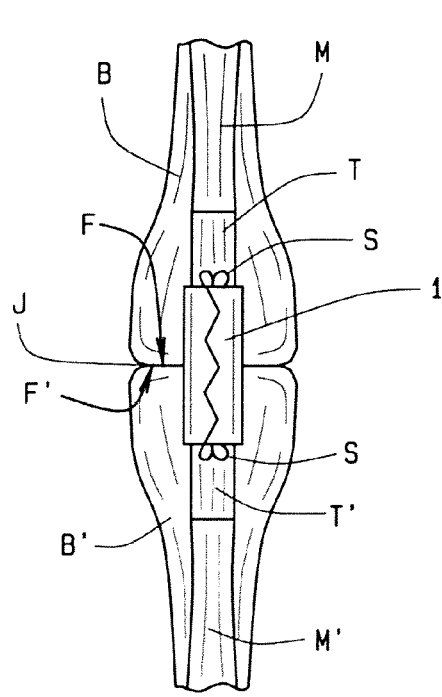
FIG. 8 shows a top view of an alternate embodiment of the present invention.

FIG. 8 then shows an alternate embodiment of the present invention 1 installed upon a tendon T, T' undergoing repair. The alternate embodiment receives the ends T, T' into each end of the device and a surgeon secures the device to each tendon end using a transfixion stitch S. The stitches S and the operation of the invention keep it upon the tendon as the tendon ends heal and naturally reconnect.

Figure 9:
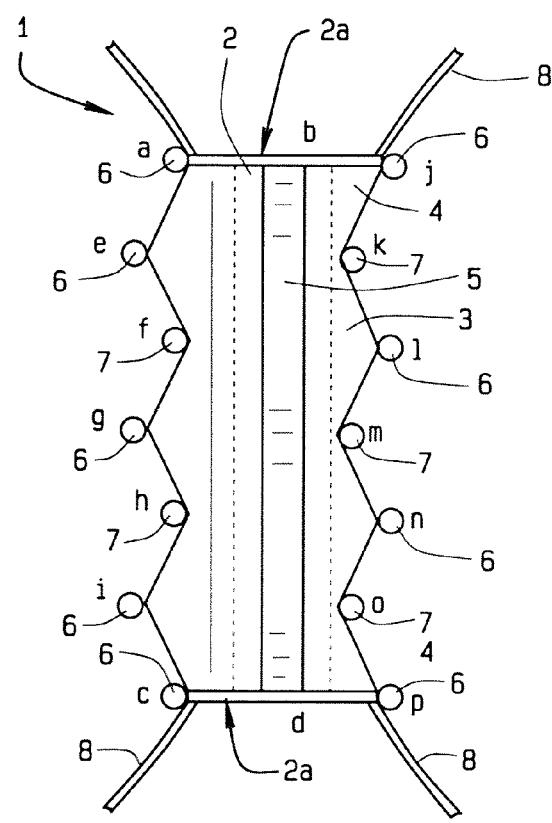
FIG. 9 illustrates a bottom view of an alternate embodiment of the present invention.

To reach the result shown in FIG. 8, the alternate embodiment of the invention begins in flat form shown in FIG. 9. The invention 1 has a generally flat form of mesh like material with two mutually parallel and spaced apart lateral ends 2, 2a, and two spaced apart opposed undulating sides. Each lateral end contains a reinforced tube like member that receives a suture 8. The undulating sides have a more rectilinear wave like form. The left side in the drawing has three flaps 3 of triangular shape while the right side in the drawing has two flaps 2 also of triangular shape offset half the length of a flap from the left side. The right side includes two half flaps 4, each locating proximate end end 2, 2a. The left side is denoted by the letters a, e, f, g, h, l, c and the right side is denoted by the letters j, k, l, m, n, o, p. The left side also includes outloops 6 shown at points a, e, g, l, c and inloops 7 shown at points f, h. The inloops occupy an interior angle between two flaps. Then upon the right side, it includes outloops 6 shown at points j, l, n, p and inloops 7 shown at points k, m, o. The flaps of the left side mate between adjacent flaps upon the right side upon rolling the device as later shown. The device includes a backer 2 generally extending lengthwise between the left side and the right side as shown. The backer extends between points b, d.

Figure 10:
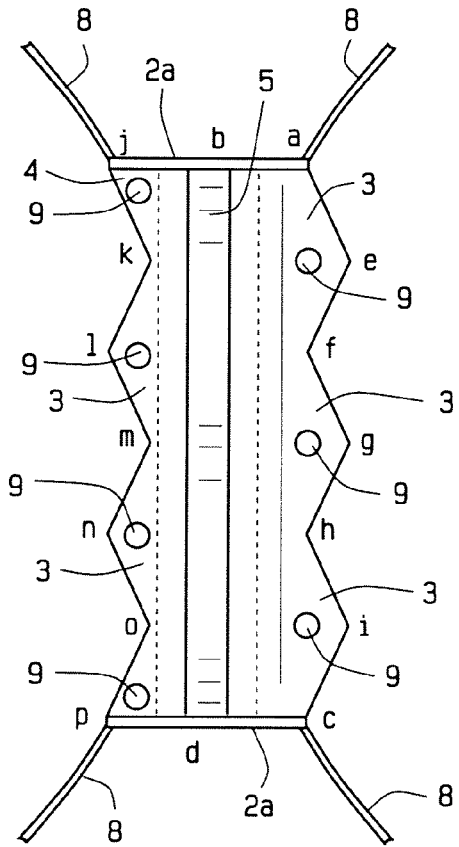
FIG. 10 illustrates a top view of an alternate embodiment of the present invention.

Turning the device over, FIG. 10 shows a bottom view of the device when in flat form. This view has the undulating patterns of each side reversed from FIG. 8. This view also shows that each flap, on both sides, includes an aperture 9. Each end 2, 2a also includes an aperture spaced outwardly from the backer towards a half flap 4. The apertures are generally inline with the outloops of the adjacent flap.

Figure 11:
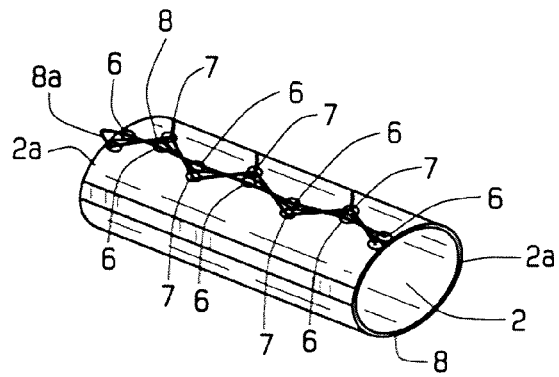
FIG. 11 provides an isometric view of an alternate embodiment of the invention rolled.

Having described the device, a surgeon places it beneath the two severed ends T, T' and inserts the ends approximately 1 centimeter inwardly upon the device. The surgeon secures the alternate embodiment of the device to each tendon with a transfixion stitch and then rolls each side of the device upwardly and around the two ends T, T' attaining the cylindrical like form shown in FIG. 11. The surgeon then extends a doubled suture through the outloops 6 and adjacent inloops 7 now adjacent to each other, in an alternating manner. The surgeon does this suture from both ends 2, 2a of the invention. With both ends sutured, the surgeon then pulls the sutures snug which closes the left side upon the right side of the invention generally above the tendon, not shown for clarity. The surgeon then takes another double suture and passes it through the outloops at each end and then the apertures in a generally spiral like manner. The surgeon pulls this other double suture and in doing so compresses the material of the device upon the tendon ends therein.

Figure 12:
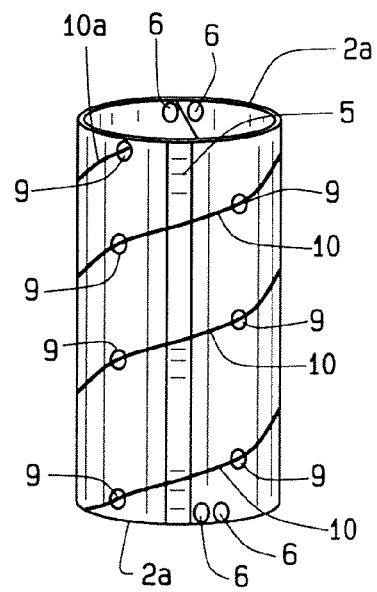
FIG. 12 provides a bottom view of the invention rolled.

FIG. 12 shows the alternate embodiment of the device upright but with the backer 2 in the foreground, that is, beneath a tendon repair. The other suture wraps about the device in a helical manner, thus facilitating compression of the tendon and improved healing thereof.

Figure 13:
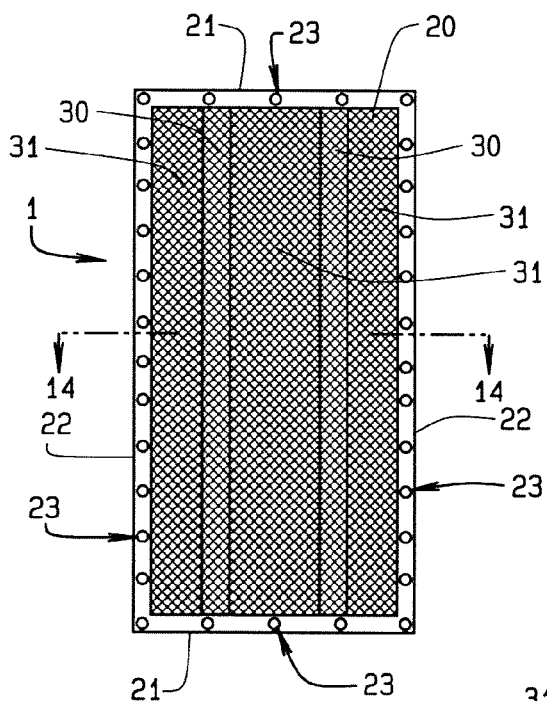
FIG. 13 shows a top view of an alternate embodiment of the present invention.

An alternate embodiment of the invention 1 appears in flat form from the top in FIG. 13. This alternate embodiment alters the mesh layer 2 so that the invention rolls into an ovoid cross section as later shown in FIG. 15. This alternate embodiment has a generally rectangular form with a mesh construction, as at 20. The invention has two mutually parallel and spaced apart lateral ends 21 and two mutually parallel and spaced apart longitudinal sides 22. The lateral ends being perpendicular to the longitudinal sides. Both the lateral ends and the longitudinal sides have a plurality of apertures 23 formed therein. Parallel to the sides, the mesh layer, as at 20, has two bands of thinner mesh as at 30. The two bands 30 are mutually parallel and extend for the length of the mesh. Between the two bands and outwardly from the bands, the mesh has a greater thickness, as at 31, typically shown as strips. The strips 31 are approximately double the thickness as the bands 30 but slightly less than the thickness of the edges of the sides 22. As before, the apertures 23, whether a puncture through reinforced edge or a grommet, receive sutures during installation of the invention upon a tendon. Approximate dimensions of the bands include 0.5 mm and of the strips includes 1.0 mm.

Figure 14:
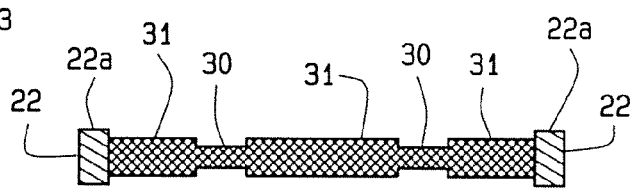
FIG. 14 describes a section view of the alternate embodiment of FIG. 13.

FIG. 14 provides a sectional view through the alternate embodiment of the mesh. The mesh has a generally rectangular cross section but upon closer inspection of this Figure, the mesh has two spaced apart sides 22. Each side has a thickness as at 22a. Inwardly from each side, the mesh 20 steps down in thickness slightly for the strips 31. The side has a smoothed transition to the adjacent strip. Inwardly from each strip, the mesh steps down again in thickness, approximately 50% for the bands 30. And inwardly from the bands, the mesh steps up in thickness back to the thickness of the strips 31. The mesh also has a smooth transition between the strips and the adjacent bands. The generally thinner bands permit the mesh to roll upwardly and inwardly and to attain and an ovoid cross section, similar to that of a tendon. The thinner bands permit the spaced apart bending of the mesh at the end of the major axis as at 25 of the ovoid shape, such as at the curved portions of the ovoid shape, while the thicker bands lessen the mesh bending at the ends of the minor axis as at 26, such as the flatter portions of the ovoid shape. The thicknesses of the bands and the strips cooperate and establish a mesh, as at 20, of differential rigidity that attains an ovoid cross section. The bands have a width of one half millimeter or multiple thereof and the strip has a width of one millimeter or multiple thereof.

Figure 15:
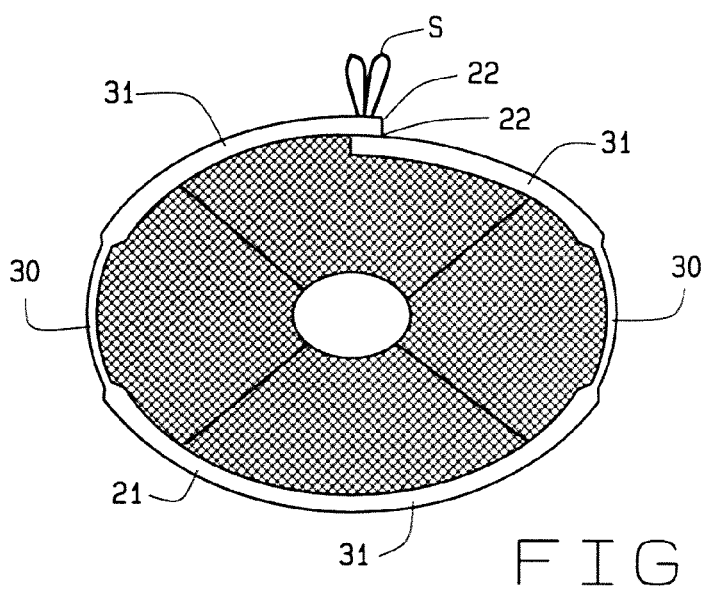
FIG. 15 shows an end view of the alternate embodiment of FIG. 13 when installed.

And, FIG. 15 provides an end view of an alternate embodiment of the invention previous shown in FIGS. 13, 14. In this view, the sides 22 are brought upwardly and inwardly by the surgeon to surround a tendon, not shown. The surgeon positions the sides 22 mutually adjacent in a butt joint, as shown, without an overlap. The surgeon then secures the sides with a suture as at S. The sutures secure the two thickened edges 22a of the mesh 20 spaced apart and opposite the centermost strip 31 so that the sutures and centermost strip define the ends of the minor axis 26 of the ovoid shape. Outwardly from the centermost strip 31, the mesh thins through the two bands 30 and the mesh rolls upwardly and inwardly utilizing its shape memory. The lesser thickness of the two bands allows the mesh to roll more tightly and transition to above the centermost strip towards the joint closed by the sutures as at S. The two bands are generally mutually spaced apart upon the ends of the minor axis 25 of the ovoid shape. The bands are somewhat perpendicular to the centermost strip 31 and the abutting sides 22 at the suture S. The ovoid shape of this alternate embodiment fits within the palmar/volar recesses established in digital and phalangeal joints.

From the aforementioned description, a flexor tendon repair device has been described. The flexor tendon repair device is uniquely capable of binding to two severed tendon ends, wrapping the repair site, and of tightening the repair upon application of an axial load. The flexor tendon repair device and its various components may be manufactured from many materials, including but not limited to, polymers, non-resorbable suture material such as nylon, polypropylene, resorbable suture material such as polygalan, Vicryl®, or polydioxane, PDS, polyvinyl chloride, high density polyethylene, polypropylene, select plant materials, such as wood or corn derived plastics, ferrous and non-ferrous metals, their alloys, and composites.

Various aspects of the illustrative embodiments have been described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations have been set forth in order to provide a thorough understanding of the illustrative embodiments. However, it will be apparent to one skilled in the art that the present invention may be practiced without the specific details. In other instances, well known features are omitted or simplified in order not to obscure the illustrative embodiments.

Various operations have been described as multiple discrete operations, in a manner that is most helpful in understanding the present invention, however, the order of description should not be construed as to imply that these operations are necessarily order dependent. In particular, these operations need not be performed in the order of presentation.

Moreover, in the specification and the following claims, the terms "first," "second," "third" and the like—when they appear—are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to ascertain the nature of the technical disclosure. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

As such, those skilled in the art will appreciate that the conception, upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

I claim:

1. A surgical repair device to abut opposed ends of a severed or ruptured tendon or ligament member during healing of said member, said surgical repair device comprising:

a sheet of nonresorable synthetic material having a semi-rigid mesh like construction, two lateral ends, two spaced apart longitudinal sides, said longitudinal sides being mutually parallel and spaced apart, said lateral ends being mutually parallel and spaced apart and perpendicular to said longitudinal sides;

at least one doubled continuous suture upon each lateral end, said at least one doubled suture being operably strong enough to carry the load of said member when in place, and each of said at least one doubled continuous suture resisting axial separation of said opposed ends during motion of said member; and, each of said sides having a pattern of apertures therein, said apertures receiving said at least one doubled continuous suture lacing through said pattern of apertures alternating from one side to the other side and extending from one lateral end to the other lateral end;

wherein said device has a generally predetermined tubular form and one of an integral oval cross section adapted to fit an anatomical shape of said member and an integral elliptic cross section adapted to fit an anatomical shape of said member, wherein said integral oval cross section has an approximate ratio of 2.5:1 for its width to its height and said integral elliptic cross section has an approximate ratio of 2.5:1 for its width to its height;

wherein upon pulling said suture, said device is adapted to roll upon said member placed therein and said device is adapted to compress said member circumferentially upon multiple locations; and wherein said device is adapted to reestablish a normal anatomic shape and dimensions of said member.

2. The surgical repair device of claim 1 further comprising:
another doubled suture upon one of said sides, said doubled suture mutually connecting said sides;
said sides adjoining each other in a butt joint; and,
said another doubled suture connecting said sides through said butt joint.

3. The surgical repair device of claim 1 further comprising:
said device having the shape of an elliptic cylinder and said device being nonresponsive to a stimulus.

4. The surgical repair device of claim 1 further comprising:
said sheet of nonresorable synthetic material having two mutually parallel and spaced apart bands, said bands being parallel to said sides, said bands having lesser thickness than the remainder of said sheet of material, and a strip located between said bands and parallel to said sides, said strip having a greater thickness than said bands, said sheet of material outwardly of said bands having similar thickness as said strip;
said sheet of synthetic material having differential rigidity and attaining an elliptic cross section when said sides mutually approach.

5. The surgical repair device of claim 4 wherein said bands have a width of a multiple of one half millimeter and said strip has a width of a multiple of one millimeter.

6. The surgical repair device of claim 1 further comprising:
said device attaining a predetermined elliptic cylindrical shape upon drawing said sides mutually together wherein said device is adapted to fit within one of a tendon sheath and a palmar/volar recess adjacent to said member.

7. The surgical repair device of claim 1 further comprising:
each of said longitudinal sides being folded inwardly thus presenting a reinforced edge;
each of said lateral ends being folded inwardly thus presenting a reinforced edge; and,
each of said apertures passing through one of said longitudinal sides and said lateral ends.

8. A surgical repair device to abut opposed ends of a severed or ruptured tendon or ligament member during healing of said member, said surgical repair device comprising:
a sheet of nonresorable synthetic material having a semi-rigid mesh like construction, two lateral ends, two spaced apart longitudinal sides, said longitudinal sides being mutually parallel and spaced apart, said lateral ends being mutually parallel and spaced apart and perpendicular to said longitudinal sides;

at least one doubled continuous suture upon each lateral end, said at least one doubled suture being operably strong enough to carry the load of said member when in place, and each of said at least one doubled continuous suture resisting axial separation of said opposed ends during motion of said member; and, each of said sides having a pattern of apertures therein, said apertures receiving said at least one doubled continuous suture lacing through said pattern of apertures alternating from one side to the other side and extending from one lateral end to the other lateral end;

wherein said device has a generally predetermined tubular form and one of an integral oval cross section adapted to fit an anatomical shape of said member and an integral elliptic cross section adapted to fit an anatomical shape of said member, wherein said integral oval cross section has an approximate ratio of 2.5:1 for its width to its height and said integral elliptic cross section has an approximate ratio of 2.5:1 for its width to its height;

wherein upon pulling said suture, said device is adapted to roll upon said member placed therein and said device is adapted to compress said member circumferentially upon multiple locations;

wherein said device is adapted to reestablish a normal anatomic shape and dimensions of said member;

another doubled suture upon one of said sides, said doubled suture mutually connecting said sides;

said sides adjoining each other in a butt joint and said another doubled suture connecting said sides through said butt joint;

said device having the shape of an elliptic cylinder and said device being nonresponsive to a stimulus, wherein said device is adapted to fit within one of a tendon sheath and a palmar/volar recess adjacent to said member;

each of said longitudinal sides being folded inwardly thus presenting a reinforced edge;

each of said lateral ends being folded inwardly thus presenting a reinforced edge; and, each of said apertures passing through one of said longitudinal sides and said lateral ends.

\* \* \* \* \*